United States Patent [19]

Hardy

[11] Patent Number: 5,003,488

[45] Date of Patent: Mar. 26, 1991

[54] AUTOMATIC FLUID SEDIMENTATION RATE MEASUREMENT APPARATUS AND METHOD

[75] Inventor: Francois Hardy, Raincy, France

[73] Assignee: Gespac, Inc., Mesa, Ariz.

[21] Appl. No.: 321,394

[22] Filed: Mar. 10, 1989

[51] Int. Cl.$^5$ .................... G06F 15/46; G01N 1/10
[52] U.S. Cl. ................. 364/509; 364/413.08; 250/573; 356/427; 356/440; 356/441
[58] Field of Search ............... 364/509, 510, 413.07, 364/413.08, 413.09; 356/440–442, 427; 250/573

[56] References Cited

U.S. PATENT DOCUMENTS

| | | | |
|---|---|---|---|
| 4,125,828 | 11/1978 | Resnick et al. | 364/413.08 |
| 4,201,470 | 5/1980 | Ehrly et al. | 356/427 |
| 4,501,491 | 2/1985 | Breda et al. | 356/440 |
| 4,609,991 | 2/1986 | Minton et al. | 364/499 |
| 4,683,120 | 7/1987 | Meserol et al. | 356/427 |
| 4,710,874 | 12/1987 | Cinqualbre | 364/413.07 |
| 4,758,083 | 7/1988 | Bellhouse et al. | 356/427 |

Primary Examiner—Parshotham S. Lall
Assistant Examiner—Brian M. Mattson
Attorney, Agent, or Firm—Harry M. Weiss

[57] ABSTRACT

An apparatus and method for automatically measuring and recording erythrocyte sedimentation rates (ESR) of blood samples according to the Westergren method includes a controllable speciment device member which measures sedimentation data of blood samples, and a data processor which controls the specimen device analyzes the sedimentation data and reports the results of its analyses. The specimen device is equipped with a controllable camera which measures the opacity of light passing through a speciment being analyzed. The camera has a high dynamic range, meaning that it is sensitive over a blood spectrum of light intensities, so that it guarantees an accurate reading even when the blood sample is hemolyzed or has turbid plasma. The apparatus makes an initial sedimentation height measurement on a specimen sample, and after a given amount of time makes a final sedimentation height measurement on that specimen. By comparing the initial and final sedimentation height measurements over a elapsed sedimentation time, the data processor calculates the sedimentation rate of the sample.

14 Claims, 4 Drawing Sheets

AUTOMATIC FLUID SEDIMENTATION RATE MEASUREMENT APPARATUS AND METHOD

FIELD OF THE INVENTION

The present invention relates to a fluid sedimentation rate measurement apparatus and method. More particularly, the present invention relates to instruments designed to automatically measure and record erythrocyte sedimentation rates (ESR) of blood samples.

DESCRIPTION OF THE PRIOR ART

To measure the ESR of a patient's blood, a laboratory technician places a sample of the patient's blood in a tube having graduated markings, records the sedimentation of corpuscular sediments at a zero time, then records the changes in sedimentation at one hour intervals as required.

This method has several drawbacks, as the readings are subject to many forms of human error by the technician. The technician may make simple, yet drastic, recording errors, such as by transposing digits or by making other similar mistakes. Even if the data are correctly recorded, the data themselves may be in error, due to inconsistent light intensity used to take the various readings. Even if the data are correctly read and recorded, they may yet be misleading. If, for example, consecutive readings are not taken at exact one hour intervals, the data will not accurately reflect the actual sedimentation rate. Finally, as the number of samples being analyzed rises, the propensity for error rises accordingly, as the technician may simply make the error of recording one patient's data on another patient's chart, or may forget to take each required reading for each sample.

Therefore, a need exists for an apparatus and method of automating the processes of performing ESR analyses and of recording the results of those analyses in order to present more accurate measurement data by minimizing the possibility of human error. A need exists for such an apparatus and method which will increase productivity by servicing more patient samples in a more efficient manner and which will produce more consistent ESR data.

SUMMARY OF THE INVENTION

It is the objective of the present invention to provide an apparatus and method for automatically performing ESR analyses on multiple blood samples and for automatically recording the results of those analyses, to eliminate or minimize human error, to increase laboratory efficiency, and to produce consistent and accurate ESR data.

The present invention discloses an automated sedimentation rate measurement system apparatus which has a controllable specimen device which measures sedimentation data of fluid samples, and a data processor which controls the specimen device, analyzes the sedimentation data, and reports the results of its analyses. The apparatus makes an initial sedimentation height measurement on a specimen sample, and after a given amount of time and several periodic measurements, it makes a final sedimentation height measurement on that specimen. By comparing the initial and final sedimentation height measurements over the elapsed sedimentation time, the apparatus calculates the sedimentation rate of the sedimentation rate of the sample.

The specimen device has a rotating drum containing a plurality of tube holders, to enable the apparatus to simultaneously measure the sedimentation rates of multiple specimen samples. The drum is driven by a controllable drum motor. Each tube holder has a top clip and a bottom support for holding a sealed, disposable specimen tube. Each holder is associated with an individual visual marker, which serves to uniquely identify the holder to a laboratory technician operating the apparatus.

For consistency in light intensity between data readings, the rotating drum is provided with a controllable light source. The light source is mounted radially inward from the tube holders, and the drum is mounted in an enclosure. The enclosure has an aesthetic cover, which allows the technician to observe the rotating tubes, and which improves data consistency by containing the light provided by the light source and by excluding ambient laboratory light. As the drum rotates, one individual specimen tube at a time will pass in front of this light source and be illuminated for analysis. The enclosure is also provided with functional internal shields for the light source, to further improve data consistency. The shields have an aperture which allows the transmitted light to escape in a controlled pattern.

Finally, the specimen device is equipped with a controllable camera which measures the light passing through a specimen being analyzed. The camera has a high dynamic range, meaning that it is sensitive over a broad spectrum of light intensities, so that it guarantees an accurate reading even when the blood sample is hemolyzed or has turbid plasma.

The data processor centers around a microprocessor and has separate control capability over the drum motor, light source, and camera of the specimen device. The microprocessor is electronically coupled to a data bus, which is in turn connected to read only memory (ROM) which contains the code defining the apparatus' operation, random access memory (RAM) which holds patient data records for a plurality of samples, an input/output (I/O) device, a clock device, and an output port.

The I/O device is equipped with a liquid crystal display, which displays a menu of the available commands. The laboratory technician selects menu options and enters data through the I/O device's keyboard. For example, the technician may enter instructions causing the data processor to start the drum rotating and to turn on the light source, if the apparatus is not already in use. When beginning the analysis of a new sample, the technician enters the patient's name and identification number, and the number of the tube holder into which he will place the tube containing the sample.

The data processing means is coupled to the drum through an optical sensor which senses the presence of a tube holder in front of the camera, and another optical sensor which senses the completion of a rotation of the drum. The signals provided by these optical sensors, combined with the new sample's data record, allow the microprocessor to determine when the tube holder containing the new sample is positioned before the camera. When this occurs, the microprocessor triggers the camera, causing it to take opacity readings from the sample tube. The opacity readings are taken by passing a constant intensity light through the sample and into an array of photoelectric diodes. The diodes produce analog signals whose intensity varies in direct proportion to the intensity of light striking the diodes. As the sediments in the fluid sample settle to the bottom of the tube, the top of the sample will become less opaque and the bottom will become more opaque. These analog signals are converted to a digital data value, representing a sedimentation height for the sample, or the highest position within the sample which is deemed to have achieved a certain opacity. This data value is returned on the bus to the microprocessor, where it may be analyzed and manipulated according to the code in ROM. Multiple readings are taken at each passage, from which the microprocessor selects a best reading according to a sedimentation algorithm in the ROM code.

When a sample makes its first pass before the camera, the apparatus takes an initial reading of the sedimentation height of the sample and stores this initial reading in memory. At the end of periods of time specified by the code in ROM, typically one hour, but less time periods such as one half hour periods may also be specified, a final sedimentation height is read from the sample. The microprocessor compares the sample's initial and final readings over the specified period of elapsed time, and calculates a sedimentation rate for the sample according to a sedimentation rate sample. The I/O device is equipped with a printer for outputting this report. Finally, the data processor is equipped with an output port which allows it to communicate with an external computer or other device, according to the ROM code.

Therefore, to the accomplishments of the foregoing objects, the invention consists of the foregoing features hereinafter fully described and particularly pointed out in the claims, the accompanying drawings and following disclosure describing in detail the invention, such drawings and disclosure illustrating, however, but one of the various ways in which the invention may be practiced.

DESCRIPTION OF THE PREFERRED EMBODIMENT

Figure 1:
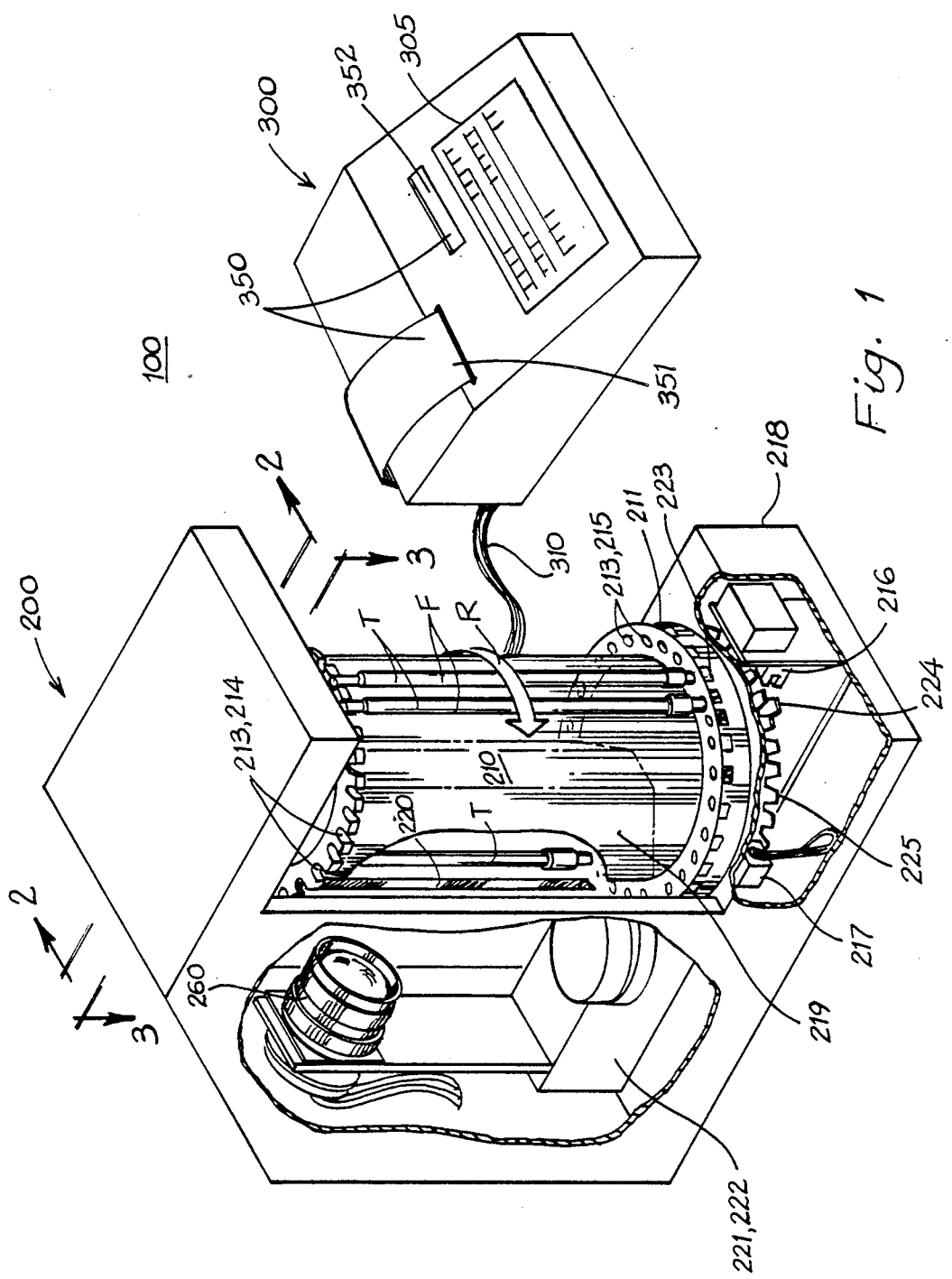
FIG. 1 is a perspective view of the automated sedimentation rate measurement system of the present invention, illustrating a controllable specimen device member provided with rotating specimen drum member and a camera coupled to a data processor equipped with an input/output device having a display, a printer, and data entry means.
Figure 2:
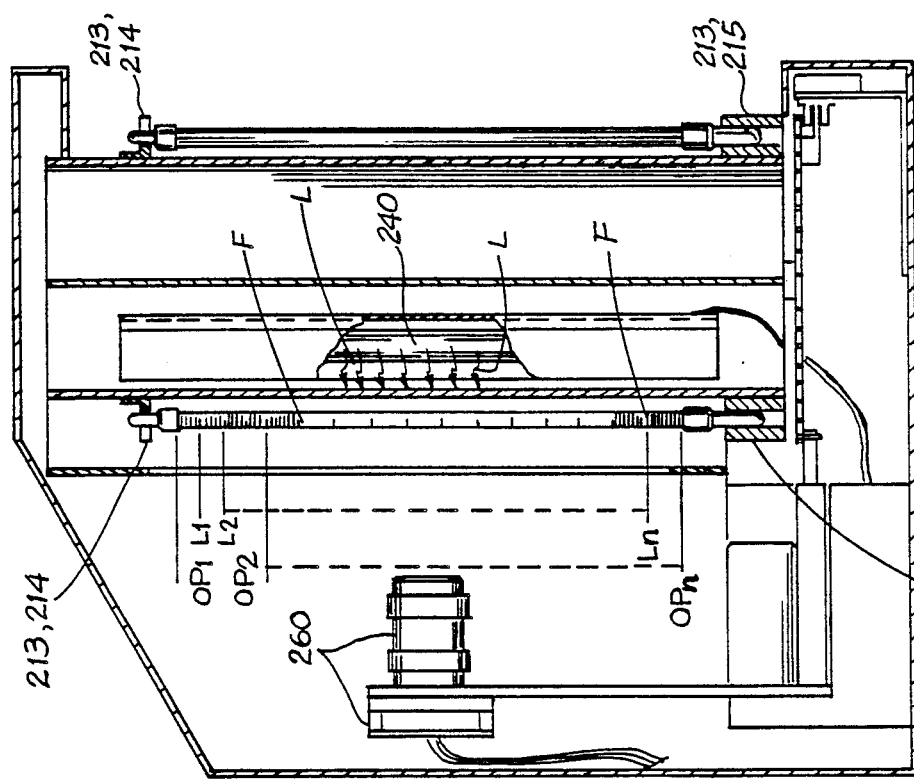
FIG. 2 is a side view of the controllable specimen device member taken along the line 2—2 of FIG. 1, illustrating the drum member, and the camera monitoring the opacity of a specimen.

FIGS. 1 and 2 illustrate the sedimentation rate measurement system apparatus 100 of the present invention, which measures the sedimentation rate of fluid samples. Although it will be described herein as analyzing blood samples, the present invention is capable of operating on a multitude of other fluids as well. The use of blood is merely for ease of description, and is not to be interpreted as limiting the scope of the invention. The primary components of the present invention are a controllable specimen device 200 and a data processor 300, which are electronically coupled via a data interface means 310.

The specimen device 200 has a tube holder means, generally designated 210, which holds a plurality of specimen tubes T, which may contain samples of fluid F to be analyzed. The sedimentation rate of a sample F is analyzed by periodically passing light L through the sample F. Sedimentation is indicated by the varying opacity OP1-OPn of the sample F from its top to its bottom. The sedimentation rate is simply determined by comparing two or more opacity observations at different points in time, typically one hour. Light L provided by light source 240 passes through a tube T, which contains a sample of fluid F to be analyzed, and the emerging light L1 to Ln is measured by a light sensing means 260.

Figure 4:
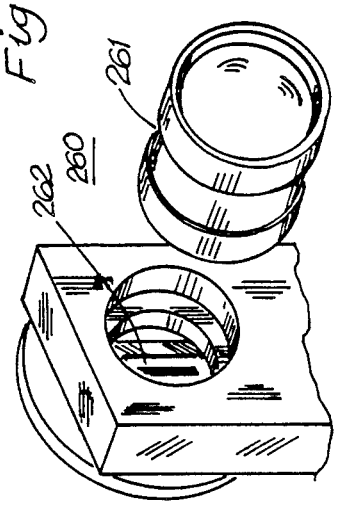
FIG. 4 is a perspective view of the photosensitive electronic means internal to the camera device.

In the best mode contemplated, the light sensing means 260 is a charge-coupled device (CCD) linear camera with 0.5 millimeter resolution and a high dynamic range. FIG. 4 illustrates this best mode, showing a lens 261 which focuses the emerging light L1 to Ln onto a CCD diode array 262, which is aligned in a vertical line. The CCD diodes are extremely photosensitive and react to various intensities of light by producing correspondingly varying voltages. Because the camera is extremely sensitive, its shutter must be synchronized to the frequency of the input AC voltage which powers the apparatus. Each time the shutter operates, it does so at precisely the same phase of the AC voltage's sinusoidal waveform, so that the light source's intensity will be identical at each shutter operation. The voltage each diode produces is an analog signal, meaning that it is taken from a continuous spectrum of voltages. The analog signal's intensity varies in direct proportion to the intensity of light striking the particular diode.

As the sediments in the fluid sample settle to the bottom of the tube T, the top of the sample F will become less opaque and the bottom will become more opaque. The upper diodes in the diode array 262 will then produce stronger voltages than those near the bottom of the array 262. The diodes 262 as a whole produce a light intensity response distribution of analog signals, which represents the varying opacity of the sample F from its top to its bottom. Camera 260 converts this plurality of analog signals into a sedimentation height measurement by a sedimentation height algorithm in analog/digital converter 263.

Figure 6:
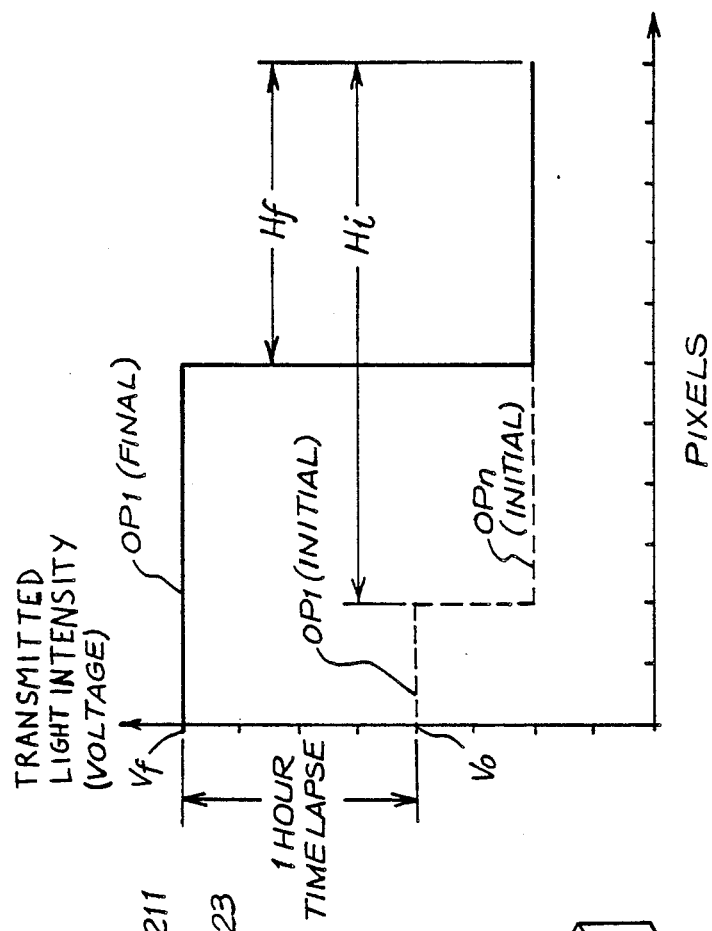
FIG. 6 illustrates a representative pixel light intensity response distribution graph associated with the opacity of a specimen at two different instances for determining the sedimentation rate of the specimen.

The fine resolution of the camera 260 enables the apparatus 100 to make detailed light transmission analyses of a sample F by taking opacity measurements at pixel intervals from the top to the bottom of the specimen; see FIG. 6 for superimposed light intensity transmission distribution graphs at an initial and final period of time. FIG. 6 shows that at initial reading, a resulting opacity of OP1(initial), may have a voltage V0 for the first few pixels of the image of tube T, then one hour later, a resulting opacity reading of OPl(final), may have a higher voltage Vf for the same few initial pixels plus several more pixels of the image of tube T due to sedimentation of the fluid in the tube. The drop in each graph indicates a substantial difference in opacity of the specimen and relates to the sedimentation height, Hi, Hf, of the specimen from which the sedimentation rate can be determined. The high dynamic range of each diode enables the camera 260 to make accurate readings of fluid samples F with a broad range of opacities OPl to OPn, even when the samples F are hemolyzed or have turbid plasma.

Tube holder means 210 is capable of holding a plurality of specimen tubes T for a plurality of patients. The tubes T are arranged circumferencially about a rotatable cylindrical drum member 211, as shown in FIG. 1. In the best modes contemplated, drum member 211 is equipped with 30 or 60 individual tube holders, generally designated 213. Drum member 211 is rotated by a drum motor member 212 (located beneath the drum member 211, but not shown in the figures). In the best mode contemplated, drum member 211 makes one complete rotation each ninety seconds. Each individual specimen tube T is held in place by an individual tube holder 213, by inserting the bottom end and top end of the tube T into a bottom support member 215 and a top clip member 214 of tube holder 213, respectively.

Figure 3:
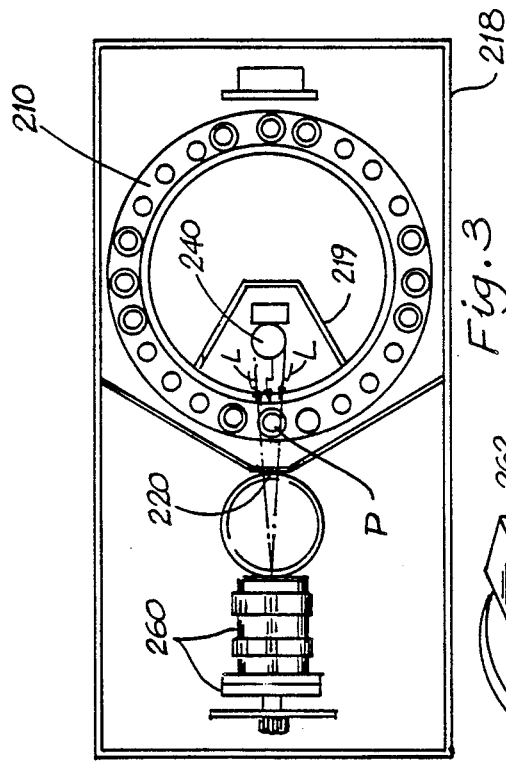
FIG. 3 is a plan view of the controllable specimen device taken along the lines 3—3 of FIG. 1, illustrating the mechanical arrangement of the light source, the specimen drum, and the camera, and the optical relationships involved in measuring the sedimentation rate of a specimen.

FIG. 3 is a cutaway top view of the controllable specimen device 200, and illustrates the alignment of its various members. Please refer to FIGS. 1, 2, and 3. The light source 240 is located within the drum member 211, radially inward from the tube holder 213. The tube holder means 210 and the camera 260 are enclosed within an exterior cover 218, which prevents the light L produced by the light source 240 from escaping, and prevents ambient laboratory light from entering, ensuring accurate analyses. To further ensure accuracy of data readings, the light source 240 is itself substantially encompassed by light shield means 219. As the drum member 211 rotates with motion R, each tube holder 213 will sequentially pass into position P, which lies directly in line with the light source 240, and the camera 260. As light L passes through a tube T in position P, the emerging light Ll to Ln may only escape the light shield means 219 through aperture 220, which lies directly between position P and the camera 260. Aperture 220 thus serves to substantially prevent the camera 260 from receiving any light other than transmitted light Ll to Ln, maximizing accuracy of readings taken by the camera 260.

To operate the apparatus 100, a laboratory technician enters commands into data input means 305 of data processor 300, which is shown in FIG. 1. In the best mode contemplated, data input means 305 is a touch sensitive membrane keyboard. These commands are displayed in menu form on a video display 352. For example, there is a menu item for a command which, when entered into data input means 305, causes data processor 300 to trigger drum motor control 380 (shown in FIG. 7), which starts drum member 211 rotating with motion R. There is also a menu item for causing data processor 300 to trigger light control 390 (shown in FIG. 7), which turns on light source 240. Drum motor control 380 and light control 390 are also capable of turning off drum motor 212 and light source 240, respectively.

When a sample of fluid F is withdrawn from a patient for analysis, it is placed into a specimen tube T. The laboratory technician selects a free tube holder 213, places the specimen tube T into it, and enters various data about the sample F into the data input means 305. This, too, is done via a menu item from display 352. In the best mode contemplated, the technician enters the patient's name and reference number, and the number of the tube holder 213 into which the specimen tube T was placed. This information makes up part of a patient data record for that particular sample F.

Figure 7:
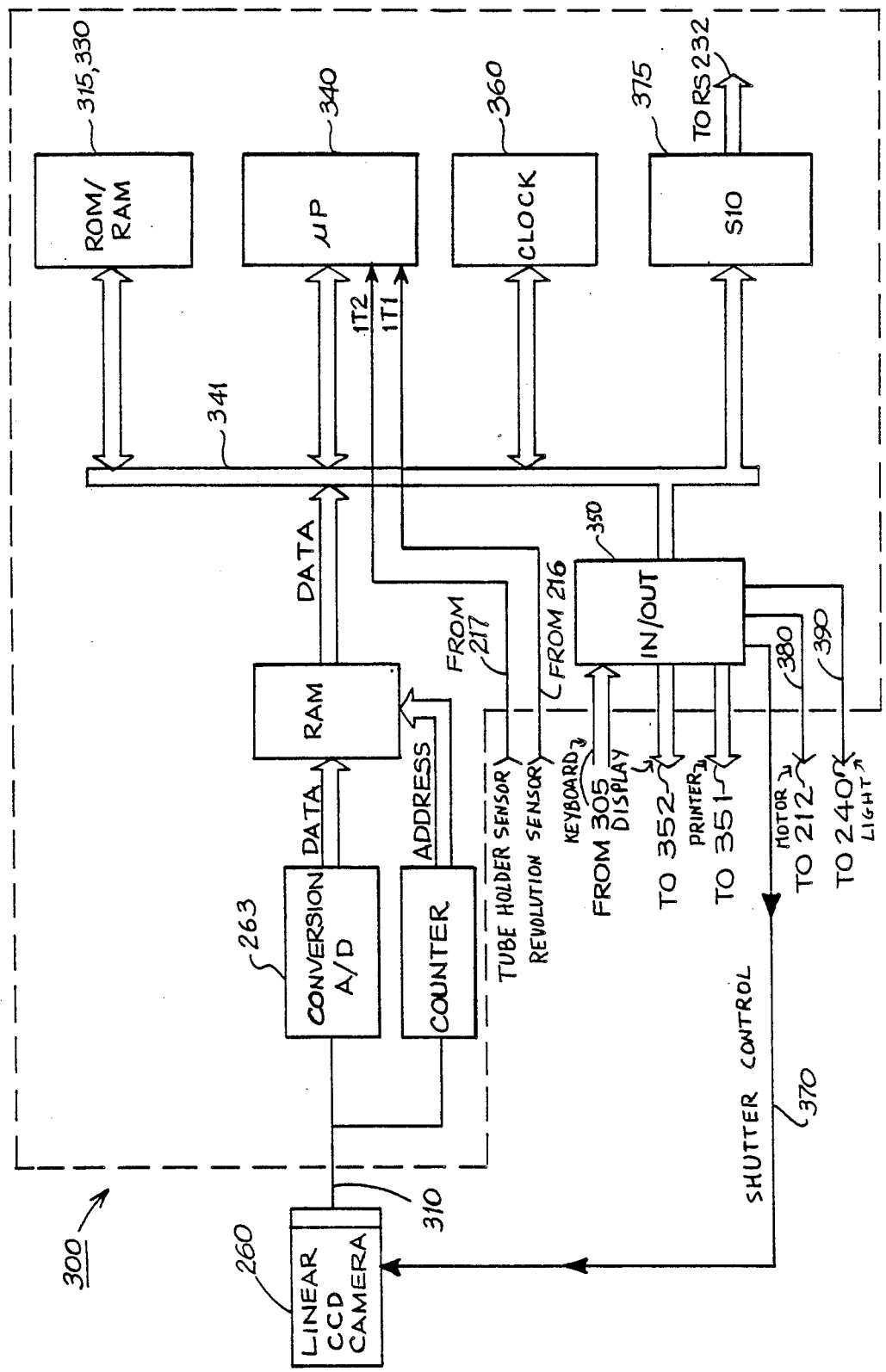
FIG. 7 is a block diagram illustrating the data flow coupling relationships between the various members of the present invention.

Please refer now to FIG. 7, which schematically illustrates additional members of data processor 300. When the technician enters the various data of the partial patient data record, they are received via bus 341 and stored in first memory means 315, which, in the best mode contemplated, is a quantity of random access memory (RAM). The operation of the data processor 300 is controlled by microprocessor code (not shown) which is stored in second memory means 330, and is executed by microprocessor 340. In the best mode contemplated, second memory means 330 is a quantity of read only memory (ROM), and microprocessor 340 is an integrated circuit chip known as a 6809.

Please refer now to FIGS. 3, 5, 6, and 7. As drum member 211 rotates with motion R, the particular tube holder 213 into which the technician has inserted the specimen tube T containing the new fluid sample F will eventually rotate into position P, where light L from light source 240 passes through the sample F, and transmitted light Ll to Ln passes through aperture 220 and into camera 260. In the best mode contemplated, camera 260 contains a photosensitive diode array 262, whose diodes produce analog voltage signals OPl to OPn in direct proportion to the intensity of the light Ll to Ln which strikes them. The plurality of such signals OPl to OPn represents the intensity transmission distribution of the light Ll to Ln passing through the sample F. Camera 260 is equipped with an analog/digital converter 263 which analyzes the instant light intensity transmission distribution and converts this distribution into an initial sedimentation height measurement Hi. Camera 260 then transmits this measurement Hi to data processor 300 via data interface 310. This initial sedimentation height measurement Hi is stored in first memory means 315, as part of the patient data record.

Figure 5:
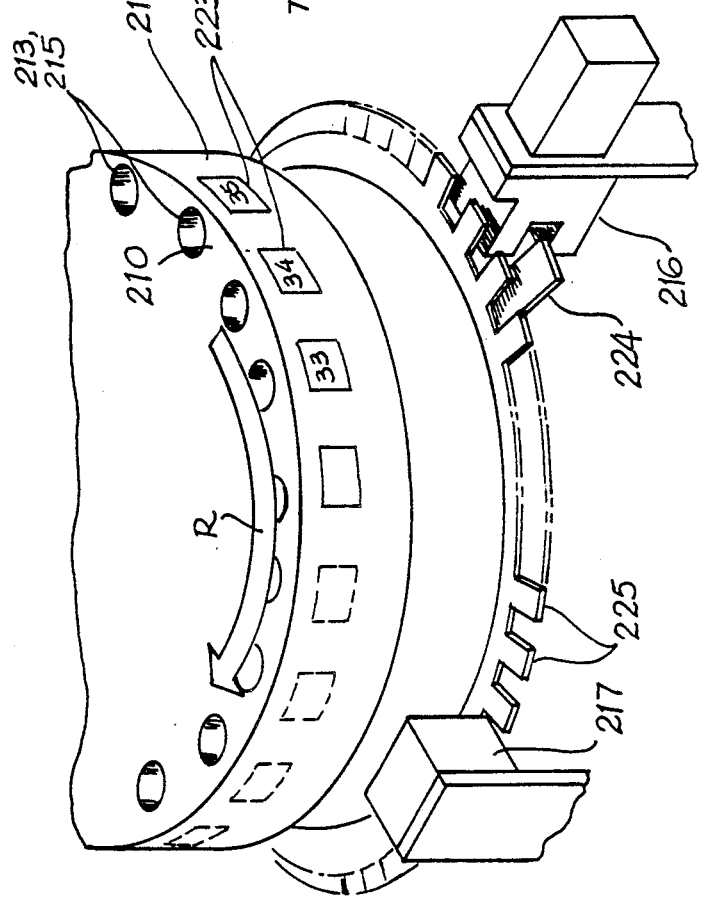
FIG. 5 is an enlarged view of the drum member of the present invention illustrating the opto-electronic sensors sensing the opaque tabs associated with the plurality of tube holder members mounted on the drum.

Each tube holder 213 is individually numbered for the technician's identification and selection, by a corresponding tube holder identifier 223 located immediately below its bottom support member 215, as shown in FIG. 5. In the best mode contemplated, tube holder identifiers 223 are simply sequentially numbered stickers. But in order for the apparatus 100 to detect when any particular tube holder 213 is in position P, tube holder means 210 is provided with revolution sensor 216 and tube holder sensor 217. Revolution sensor 216 senses an opaque revolution tab 224 which is attached to, and rotates with, drum member 211, and tube sensor 217 senses every tube holder opaque tab 225 associated with a tube holder 213 in position P. As the drum member 211 rotates, opaque tabs 224 and 225 will eventually pass by their respective sensors 6, 217. In the best mode contemplated, opaque tabs 224,225 merely breaks a beam of light within sensors 216,217, much like an entering customer breaks a beam across the doorway of a convenience store. Sensor 216,217 are of a similar construction. The opaque tabs 225 are positioned vertically above opaque tab 224, such that opaque tabs 224 and 225 will not break the beams of light within the other's respective opto-electronic sensing circuitry.

As opaque tab 224 breaks the beam within revolution sensor 16, the revolution sensor circuitry sends a signal IT1 to microprocessor 340, indicating that another revolution of drum member 211 is beginning. As each successive opaque tab 225 breaks the beam within tube sensor 217, tube sensor circuitry sends a signal IT2 to microprocessor 340, indicating that the tube in position P is the one whose sedimentation data is to be recorded. Microprocessor 340 contains initial set-up information to uniquely identify any tube specimen currently in position P as being the one that relates to opaque tab 225 being sensed by sensor 217. In the best mode contemplated, the set-up information is simply a mathematical adjustment of the microprocessor's 340 counting scheme for the signals IT1 and IT2, which takes into account the number of tube holders 213 between revolution sensor 216 and position P and that opaque tab 225 being sensed by sensor 217 relates to the tube holder and tube specimen in position P.

Because not all tube holders 213 will necessarily contain specimen tubes T, microprocessor 340 uses the data which the technician entered in order to determine which tube holders 213 are occupied at any given time. If there is a particular patient data record indicating that its sample F is in the particular tube holder 213 currently occupying position P, microprocessor 340 electronically triggers camera control 370, which causes camera 260 to operate and take a sedimentation height data reading of the sedimentation of sample F. In the best mode contemplated, eight such readings are taken, and microprocessor 340 selects a best reading from them, according to the microprocessor code.

Data processor 300 also has a clock 360, which provides microprocessor 340 with timing pulses for use by the various circuitry as well as identifying the current time of day. When particular sample F is in position P, ready for analysis, microprocessor 340 obtains the current time of day from the clock 360. If the patient data record for sample F indicates that no initial sedimentation height has been measured for sample F, then sample F is about to be analyzed for the first time, so the current time of day is recorded into the patient data record for sample F as its beginning time. At each subsequent reading of the particular sample F, the current time of day is compared to the beginning time for that particular sample F. At the end of an amount of time determined by the microprocessor code, a final sedimentation height reading is taken and recorded, and the analysis may be finished. In the best mode contemplated, final readings are taken after one hour of sedimentation, and, optionally, again after two hours of sedimentation. By comparing the initial sedimentation height measurement Hi to the final sedimentation height measurement Hf over the elapsed time of sedimentation, microprocessor 340 determines the sedimentation rate of the particular sample F, see FIG. 6.

Microprocessor 340 then generates a report for the particular patient's sample F, indicating the sedimentation rate of the sample F. The I/O device 350 of data processor 300 is equipped with data output means 351, which is a printer in the best mode contemplated. Microprocessor 340 may direct the report to the printer 351, which produces a permanent paper hard copy of the report. The report may also be directed to the display 352, where it is temporarily displayed for the technician, but in the best mode contemplated, display 352 is primarily used to display the menu of control options, as described above.

Data processor 300 is also equipped with a communication port 375, via which data processor 300 may communicate with other computers or devices. In the best mode contemplated, communication port 375 is a standard serial port known as an RS232.

Data processor 300 and specimen device 200 are powered by power converter 221, shown in FIG. 1. Power converter 221 is connected to an external electrical power source (not shown), and converts the external electricity to forms usable by the apparatus 100. In the best mode contemplated, power converter 221 is adapted for use with standard 110 or 220 volt AC power, and is equipped with a back-up battery 222 which provides power to microprocessor 340, clock 360, and first and second memory means 315 and 330 in the event of failure of the external electricity source. Back-up battery 222 enables the maintenance in status quo of the time of day, and the patient record and current stage of analysis of each of the various samples F being analyzed, so that when external power is restored, analyses will continue.

Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus.

I claim:

1. A sedimentation rate measurement apparatus for measuring a sedimentation rate of a fluid in a specimen tube, said apparatus comprising:

a controllable specimen device member; and data processor means operatively coupled to said specimen device member (i) for receiving sedimentation measurements produced by said sedimentation device member, (ii) for controlling said specimen device member and (iii) for generating sedimentation rate data of said fluid, wherein said specimen device member includes:

(1) light source means for illuminating said fluid, (2) light sensing means for responding to light transmitted from said light source means through said fluid and periodically producing sedimentation measurements for determining a sedimentation rate of said fluid, and (3) tube holder means including a member (211) disposed between the light source means and the light sensing means for holding a specimen tube in which said fluid is contained, and wherein said data processor means includes:

(a) data input means for entering specimen control data;

(b) data intereface means for receiving said sedimentation measurement data from said specimen device member;

(c) first memory means for storing said specimen control data and said sedimentation measurement data;

(d) microprocessor code means including microprocessor code for controlling operation of said specimen device member;

(e) second memory means for storing said microprocessor code;

(f) microprocessor means for performing calculations and analyses on said sedimentation measurement data and specimen control data in a manner computationally determined by said microprocessor code means; and (g) data output means for producing results of said calculations and analyses.

2. The sedimentation rate measurement apparatus of claim 1, wherein:

said tube holder means includes a rotatable cylindrical drum member, a drum motor member operatively coupled to said drum member, a plurality of tube holder members, each of said tube holder members having a top clip member and a bottom support member and being circumferentially attached about said drum member.

3. The sedimentation rate measurement apparatus of claim 2, wherein said rotatable cylindrical drum member further includes:

revolution sensor means for repeatedly sensing a completed revolution of said drum member;

tube holder sensor means for signaling that a particular tube holder is in substantial alignment with said light sensing means.

4. The sedimentation rate measurement apparatus of claim 3 wherein:

said microprocessor code means includes drum motor control means for controlling operation of said drum motor member.

5. The sedimentation rate measurement apparatus of claim 1, wherein:

said light sensing means comprises a charge coupled device linear camera.

6. The sedimentation rate measurement apparatus of claim 5 wherein:

said microprocessor code means includes camera control means for controlling said light sensing means, said camera control means operatively coupled to said tube holder sensor means such that said camera control means causes said light sensing means to operate only when said tube holder is in substantial alignment with said light sensing means and said light source means.

7. The sedimentation rate measurement apparatus of claim 1 wherein:

said microprocessor code means includes having light control means for turning said light source means on and off.

8. The sedimentation rate measurement apparatus of claim 1 wherein said specimen device member further comprises:

power converter means coupled to said data processor means and to said specimen device means for powering said data processor means and said specimen device member, said power converter means comprising back-up battery means for maintaining in memory said specimen control data and said sedimentation measurement data, and for enabling continuing operation of said clock means in the event of intermittent power failure.

9. A sedimentation rate measurement apparatus for measuring a sedimentation rate of a fluid in a specimen tube, said apparatus comprising:

a controllable specimen device member; and data processor means operatively coupled to said specimen device member (i) for receiving sedimentation measurements produced by said sedimentation device member, (ii) for controlling said specimen device member and (iii) for generating sedimentation rate data of said fluid, wherein said specimen device member includes:

(1) light source means for illuminating said fluid, (2) light sensing means for responding to light transmitted from said light source means through said fluid and periodically producing sedimentation measurements for determining a sedimentation rate of said fluid, and (3) tube holder means including a member (211) disposed between the light source means and the light sensing means for holding a specimen tube in which said fluid is contained, and wherein said specimen device member further comprises:

covering means for enclosing said specimen device member;

light shield means for confining said light source means within said cover means and for excluding ambient laboratory light; and aperture means disposed between said light source means and said light sensing means for allowing said light to escape said shield means in a pattern directed toward said light sensing means.

10. A method of obtaining sedimentation rate data of a fluid, said method comprising the steps of:

(a) providing a specimen device member, said specimen device member having, tube holder means for holding a specimen tube, light source means disposed within the tube holder means for illuminating said specimen tube, light sensing means for responding to light transmitted from said light source means through said specimen tube and for producing sedimentation measurements according to opacity of said transmitted light and means disposed in proximity with said light source means and with said light sensing means for impeding the transmission, beyond the specimen device member, of light that emanates from the light source means and for impeding the transmission, into the specimen device member, of ambient light;

(b) operatively coupling a data processor member to said specimen device member; and (c) generating sedimentation rate data from said sedimentation measurements produced by said light sensing means, said method further comprising the steps of:

providing said tube holder means as a rotatable cylindrical drum member;

operatively coupling a drum motor means to said drum member for rotating said drum member;

attaching a plurality of tube holder members about a circumference of said drum member;

providing said drum member with revolution sensor means for repeatedly sensing a completed revolution of said drum member and for providing a signal indicating each completed revolution; and providing said drum member with a tube holder sensor means for repeatedly sensing substantial alignment of each tube holder member of said plurality of tube holder members with said light sensing means, and for providing a signal indicating each substantial alignment, and wherein said data processor means includes:

(d) data input means for entering specimen control data;
(e) data interface means for receiving said sedimentation measurement data from said specimen device means;
(f) first memory means for storing said specimen control data and said sedimentation measurement data;
(g) microprocessor code means for controlling operation of said specimen device member;
(h) second memory means for storing said microprocessor code means;
(i) microprocessor means for performing calculations and analyses on said sedimentation measurement data and specimen control data in a manner computationally determined by said microprocessor code means; and
(j) data output means for producing results of said calculations and analyses.

11. The method of claim 10 further comprising the steps of:
filling said specimen tube with a first sample of said fluid;
selecting a first tube holder member from said plurality of tube holder members;
placing said specimen tube into said first tube holder member;
entering a first partial patient data record for said first sample into said data input means, said partial patient data record comprising information identifying said first sample and said first tube holder member;
storing said first partial patient data record into said first memory means;
waiting until said revolution sensor means provides a signal indicating the completion of a complete revolution of said drum member;
initializing a tube holder count at zero;
counting each signal provided by said tube holder sensor means until said tube holder count corresponds with said information identifying said first tube holder member;
measuring said light transmitted from said light source means through said specimen tube and into said light sensing means;
producing a first sedimentation measurement according to said measuring step; and
entering said first sedimentation measurement into said first partial patient data record in said first memory means.

12. The method of claim 11 further comprising the steps of:
continuing rotation of said drum member for a first sedimentation time determined by said microprocessor code means;
repeating said waiting, initializing, counting, and measuring steps, in order, once each;
producing a second sedimentation measurement according to said measuring step;
comparing said first and second sedimentation measurements to produce a first sedimentation amount;
calculating a first sedimentation rate for said first sample, according to said first sedimentation amount and said first sedimentation time; and
reporting said first sedimentation rate.

13. The method of claim 11 wherein said first sedimentation time is one (1) hour.

14. The method of claim 11 wherein said first sedimentation time is one half (½) hour.

* * * * *